(12) United States Patent
Cuppens (10) Patent No.: US 9,695,466 B2
(45) Date of Patent: Jul. 4, 2017

(54) METHODS TO REDUCE REPEATS OF IDENTICAL NUCLEOTIDES IN COPIES OF A TARGET DNA MOLECULE INCLUDING SUCH REPEATS

(71) Applicant: Harry Cuppens, Brussels (BE)

(72) Inventor: Harry Cuppens, Brussels (BE)

(73) Assignee: DNAME-IT, Leuven (BE)

( * ) Notice: Subject to any disclaimer, the term of this patent is extended or adjusted under 35 U.S.C. 154(b) by 373 days.

(21) Appl. No.: 14/274,168

(22) Filed: May 9, 2014

(65) Prior Publication Data
US 2014/0242576 A1    Aug. 28, 2014

Related U.S. Application Data

(63) Continuation-in-part of application No. PCT/EP2012/072258, filed on Nov. 9, 2012.

(30) Foreign Application Priority Data

Nov. 10, 2011    (GB) .................................. 1119390.1

(51) Int. Cl.
*C12P 19/34*    (2006.01)
*C12Q 1/68*    (2006.01)

(52) U.S. Cl.
CPC .......... *C12Q 1/6806* (2013.01); *C12Q 1/6853* (2013.01); *C12Q 1/6869* (2013.01)

(58) Field of Classification Search
USPC ..................................... 435/6.12, 91.1, 91.2
See application file for complete search history.

(56) References Cited

U.S. PATENT DOCUMENTS

| | | | |
|---|---|---|---|
| 6,150,100 A | 11/2000 | Rueschoff et al. | |
| 2010/0120097 A1 | 5/2010 | Matz et al. | |
| 2010/0205204 A1* | 8/2010 | Gojobori ................ | G06F 19/22 707/769 |

FOREIGN PATENT DOCUMENTS

| | | |
|---|---|---|
| EP | 1207210 A1 | 5/2002 |
| EP | 1650311 A1 | 4/2006 |
| WO | WO-00/20630 A1 | 4/2000 |
| WO | WO-02/22879 A2 | 3/2002 |
| WO | WO-2009/148560 A2 | 12/2009 |
| WO | WO-2013/068528 A1 | 5/2013 |

OTHER PUBLICATIONS

International Search Report for International Application No. PCT/EP2012/072258, mailed Jan. 24, 2013.
Search Report for Great Britain Application No. GB1119390.1, dated Apr. 12, 2013.
(Continued)

*Primary Examiner* — Kenneth Horlick
(74) *Attorney, Agent, or Firm* — Clark & Elbing LLP (57) ABSTRACT

The invention relates to methods to reduce the length of a homonucleotide repeat sequence a target DNA sequence. This is done by using an oligonucleotide primer which extends in the unaltered repeat of identical nucleotides of the target polynucleotide, the oligonucleotide primer comprises at the at the 5' side a sequence which hybridizes with the sequence preceding the targeted sequence repeat, but the oligonucleotide primer is not 100% complementary with the sequence repeat in the target sequence.

12 Claims, 8 Drawing Sheets

(56) References Cited

OTHER PUBLICATIONS

Written Opinion of the International Searching Authority for International Application No. PCT/EP2012/072258, mailed Jan. 24, 2013.

Clarke et al., "PCR amplification introduces errors into mononucleotides and dinucleotide repeat sequences," Mol Pathol. 54:351-353 (2001).

Fazekas et al., "Improving sequencing quality from PCR products containing long mononucleotide repeats," *Bio Techniques* 48:277, 278, 280, 282, 285 (2010).

Hale et al., "Next-generation pyrosequencing of gonad transcriptomes in the polyploid lake sturgeon (*Acipenser fulvescens*): the relative merits of normalization and rarefaction in gene discovery," BMC Genomics 10:203 (2009).

Meyer et al., "Sequencing and de novo analysis of a coral larval transcriptome using 454 GSFlx," BMC Genomics 10:219 (2009).

Murray et al., "Assays for determining poly(A) tail length and the polarity of mRNA decay in mammalian cells," Methods Enzymol. 448:483-504 (2008).

Zirvi et al., "Ligase-based detection of mononucleotide repeat sequences," Nucleic Acid Res. 27:e40 (1999).

\* cited by examiner

METHODS TO REDUCE REPEATS OF IDENTICAL NUCLEOTIDES IN COPIES OF A TARGET DNA MOLECULE INCLUDING SUCH REPEATS

FIELD OF THE INVENTION

The present invention relates to methods for determining the number of nucleotides in homonucleotide stretches.

The present invention relates to the field of so-called next generation sequencing methods.

BACKGROUND OF THE INVENTION

DNA (deoxyribonucleic acid) is the universal carrier of genetic information. DNA is an intertwined helix of two polymeric strands, each strand build-up of nucleotide units attached to a backbone of deoxyribose sugars and phosphate groups joined by ester bonds. These two strands run in opposite, anti-parallel directions. Each DNA strand is build-up of 4 nucleotides A, C, G and T, in a specific order for that DNA molecule. It is the sequence of these four bases along the backbone that encodes genetic information.

The two DNA strands have a complementary nature. An A nucleotide forms a base pair with a T nucleotide in the opposite strand, and vice versa; a G nucleotide forms a base pair with a C nucleotide in the opposite strand, and vice versa.

In eukaryotic cells, DNA is transcribed to RNA (ribonucleic acid). RNA molecules are rather similar to DNA molecules, the single chains of nucleotides are attached to a backbone of ribose sugars and phosphate. Depending on their function, there are different types of RNA molecules. mRNA molecules are used by cellular organisms to carry the genetic information encoded in DNA to direct synthesis of proteins. In some viruses, RNA is even used as the genetic code instead of DNA.

DNA can be replicated by DNA polymerases. A DNA polymerase can only extend an existing DNA strand paired with a template strand. It cannot begin the synthesis of a new strand as such. To begin synthesis, a short fragment of DNA, an oligonucleotide or RNA molecule, called a primer, must be created and paired with the template DNA strand.

Figure 1:
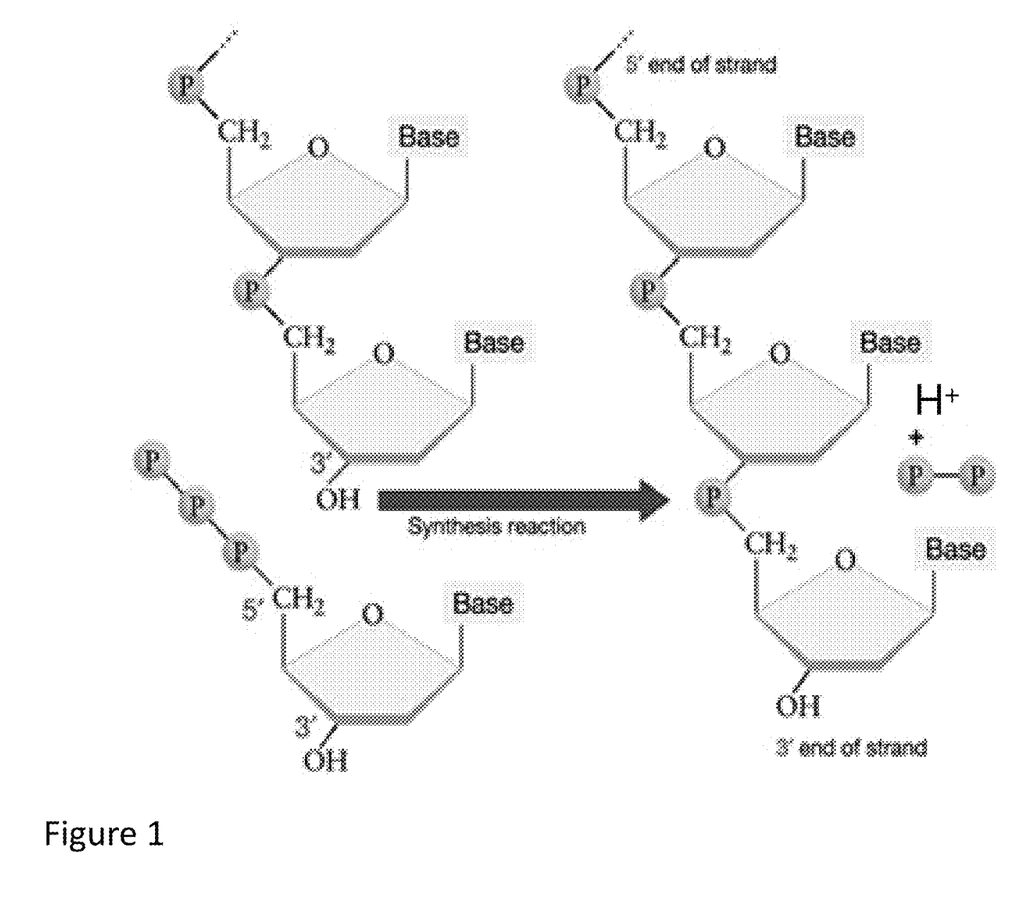
FIG. 1: Synthesis of a new DNA strand. A pyrophosphate is released from the incoming new nucleotide, and a proton is released from the extending DNA strand.

DNA polymerase synthesizes a new strand of DNA by extending the 3' end of an existing nucleotide chain, adding new nucleotides to the template strand one at a time through the creation of phosphodiester bonds. The incoming building blocks are the nucleoside triphosphates (dNTPs: dATP, dCTP, dGTP, dTTP). The oxygen of the 3'-hydroxyl end of the growing DNA strand makes a nucleophilic attack on the alpha phosphate (the one closest to the sugar) of the dNTP. The result is that the dNMP (deoxyribonucleoside monophosphate, or nucleotide) becomes covalently bound to the 3' carbon of the sugar at the end of the DNA strand, thus lengthening the strand by one nucleotide. Moreover, pyrophosphate and a proton are released (FIG. 1). Then the process repeats.

There is a huge interest in determining genetic DNA information, such as the nucleotide found at a given position, the sequence order found at given locus/loci in the genome, or even the complete genome. Even RNA can be sequenced when it is first converted to cDNA. Genetic information is determined by sequencing technologies, such as Maxim-Gilbert sequencing, Sanger sequencing and derivatives thereof, parallel pyrosequencing (Roche 454 Life Sciences), reversible terminator-based sequencing by synthesis (Illumina), Sequencing by Oligonucleotide Ligation and Detection (SOLiD) (Life Technologies), Ion Semiconductor Sequencing (Ion Torrent, Life Technologies), Single Molecule Real Time sequencing (SMRT) based on zero-mode waveguides properties (Pacific Biosciences), nanopore sensing (Oxford Nanopore Technologies), etc. Depending on the sensitivity of many sequencing technologies, pools (clones) of identical DNA molecules are sequenced in parallel. Sequencing of single DNA strands in parallel is only possible by Single Molecule Real Time sequencing and nanopore sensing. In most sequencing technologies, a double-stranded DNA molecule is denatured, and one of these single-stranded DNA molecules is then sequenced. In essence, this single DNA strand is used as a template in a sequencing reaction for the synthesis of a second complementary DNA strand, based on the complementary nature of DNA. A new DNA strand can be synthesized when a small DNA fragment, an oligonucleotide, binds to the DNA template. This oligonucleotide is a primer for further extension of a new growing DNA strand by incorporation of nucleotides on the complementary principle. Such oligonucleotides are typically about 10-25 nucleotides long and can be easily synthesized. By monitoring the synthesis of this new DNA strand, i.e. the order in which nucleotides are incorporated in the new DNA strand, the DNA sequence of that strand can be determined. Given the complementary nature of the two DNA strands, the sequence of the other original DNA strand is then also known.

Despite the progress in sequencing techniques, the sequence of the number of nucleotides in homonucleotide stretches cannot be accurately determined with certain newer generation sequencing technologies. For example pyrosequencing was invented in the early nineties, highly parallel sequencing was introduced in 2005, while Ion Semiconductor sequencing was only introduced in 2009. The pitfall of inaccurate calling of homonucleotide stretches is already known for almost two decades.

SUMMARY OF THE INVENTION

In this invention, the length of longer homonucleotide stretches is reduced to a series of shorter nucleotide parts; either both parts are shorter nucleotide stretches, or one part is a shorter nucleotide stretch and the second part is only 1 nucleotide long. For example when a stretch of 8 T residues is modified at the 7th position, the above indicated shorter nucleotide stretch contains 6 T nucleotides and the T at the 8th position represents the above mentioned "second part of only 1 nucleotide long". Both shorter nucleotide parts can be more accurately determined, and the combined accurate analysis of the smaller parts allows more accurate determination of the length of the original longer homonucleotide stretch.

A first aspect of the invention relates to methods of generating one or more copies of a target polynucleotide molecule, or part thereof, that contains a repeat of identical nucleotides. These methods comprise the steps of:
  altering one nucleotide in this repeat of identical nucleotides, or
  altering different single nucleotides separated at intervals in said repeat of identical nucleotides into another nucleotide, in order to divide said repeat of identical nucleotides into two or more smaller altered parts of identical nucleotides in the copied molecules, wherein an oligonucleotide is used for this purpose which extends in the unaltered repeat of identical nucleotides, either until the end of the unaltered repeat of identical nucleotides or not, and wherein said oligonucleotide primer is not 100% complementary within the sequence complementary to the repeat in the target sequence. The primer comprises at the at the 5' side a sequence which hybridizes with the sequence preceding the targeted sequence repeat side.

This part of the primer which hybridizes with the non-repetitive sequence provide the required specify to allow binding of the primer to the desired part of the genomic DNA sequence. In this part of the primer preceding the targeted sequence repeat side, a few mismatches (1, 2 or 3) with the template sequence are tolerable as long these mismatches do not compromise the hybridization of the primer to the target DNA.

Figure 4:
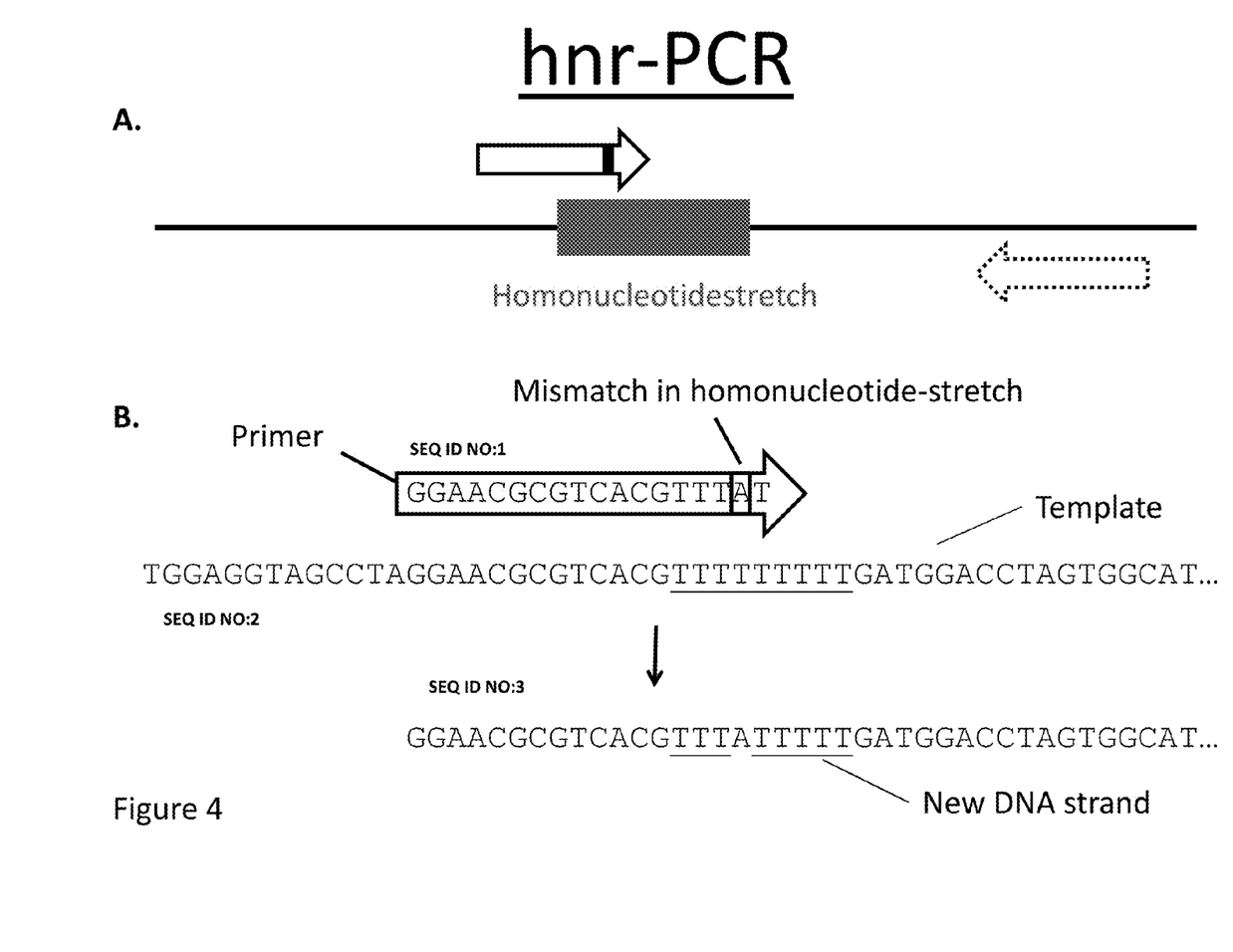

In other words as illustrated in FIG. 4, the primer which is used which hybridizes with a part of the homonucleotide stretch in the target molecule, but does not hybridize completely with the homonucleotide stretch in the target molecule. Within the portion of the oligonucleotide primer hybridizing to the homonucleotide stretch in the target molecule, at least one mismatch is incorporated, compared to the homonucleotide stretch in the target molecule. Typically, the polynucleotide is DNA.

In certain embodiments of these methods, the smaller altered parts of identical nucleotides are generated through an enzymatic or chemical reaction, such as DNA synthesis, ligation and/or amplification, or a combination thereof.

In certain embodiments of these methods, one nucleotide in the repeat of complementary identical nucleotides of the primer is replaced by another nucleotide type so that the unaltered repeat of consecutive number of identical nucleotides is split in two shorter altered parts of these identical nucleotides interrupted by the replaced nucleotide type.

In certain embodiments of these methods the part of identical nucleotides at the 3' of the primer is shorter than the part of identical nucleotides at the 5' end of the primer.

In certain embodiments of these methods, several single nucleotides in the primer in the repeat of complementary identical nucleotides are replaced at regular intervals so that all shorter parts of identical nucleotides do not exceed a given length for example not longer than 5, 6 or 7 nucleotides.

In other embodiments of these methods the obtained shorter part of identical nucleotides is no longer than 4-6 nucleotides.

In particular embodiments, the primer contains in addition at the 5' end one or more adapter nucleotides which are not complementary to the target sequence. These adapter nucleotides can be used for discriminating them from other fragment types and/or for further processing such as amplification, sequencing, inclusion of bar code sequences.

In certain embodiments of these methods different DNA synthesis/ligation/amplification reactions of the same type, or of different types, are combined in a multiplex(-like) format.

In certain embodiments of these methods, one type of the amplicons are classical amplicons, and the other type of amplicons or hnr-amplicons.

In certain embodiments of these methods all classical and hnr-primers are combined in a single reaction. The hnr-primer can either have a different concentration, melting temperature, or both, than the classical primers.

In certain embodiments, hnr-primers are added serially to the reaction mixture, i.e. after the classical amplification such as PCR has been (partly) performed and in which the classical amplicons become the template for hnr-priming and hnr-PCR. The hnr-primer can either have a different concentration, melting temperature, or both, than the classical primers.

In specific embodiments all classical primers are combined in a reaction, and all hnr-primers are combined in another reaction, and which are afterwards mixed. The hnr-primer can either have a different concentration, melting temperature, or both, than the classical primers.

Different types of primers can contain a different type of 5' adapter nucleotides which are not complementary to the target sequence.

For example the classical primers contain one type of 5' adapter nucleotides and the hnr-primers contain a different type of 5' adapter nucleotides.

A second aspect of the invention relates to a method for determining the number of nucleotides in a nucleotide repeat of a template DNA molecule in which the sequence of a copied DNA molecule is determined by sequencing, and which uses the prior knowledge of the altered nucleotides and positions generated in the copied molecules as described in the above cited methods of the first aspect, comprising the step of counting the number of identical nucleotides in the generated smaller parts and substituted nucleotides for generating the smaller parts of identical nucleotides.

Counting is most important for the last shorter part, not necessary for the other part were it can be assumed because they are provided by the primer for which you already known the exact count, even if it is much longer than 7 nucleotides. Optionally, these methods further comprise the step of performing a method of determining the qualitative nature of the stretch of identical nucleotides and its downstream and upstream DNA regions, wherein the fragments obtained from each method are discriminated and separately analyzed using said adapter sequences.

A further aspect of the invention relates to a data carrier comprising program instructions for analyzing and providing the results of the above described method, when executed on a computer.

A further aspect of the invention relates to the use of one or more oligonucleotides in a DNA synthesis, ligation, or amplification reaction to reduce larger repeats of identical nucleotides in two or more smaller parts of identical nucleotides in a method as described above.

BRIEF DESCRIPTION OF THE DRAWINGS

The application file contains at least one drawing executed in color. Copies of this patent or patent application with color drawings will be provided by the Office upon request and payment of the necessary fee.

Figure Legends:

FIG. 4: A. hnr-PCR, in accordance with an embodiment of methods of the present invention, in which one of the primers extends in the homonucleotide stretch of interest. B. Example of hnr-PCR, in accordance with an embodiment of methods of the present invention, in which the homonucleotide stretch contains a stretch of 9 T-residues. The hnr-PCR-primer extends 5 nucleotides in the homonucleotide stretch, and contains a mismatch at position 4 at the site of the homonucleotide stretch. After synthesis of a new DNA strand, a homonucleotide stretch of 3 T-residues and 5 T-residues, separated by one A-nucleotide will be obtained. When after sequencing 5-T nucleotides are found in the last 3' stretch, the original stretch contained 9 T-nucleotides; if 4-T nucleotides are found in the last stretch, the original stretch contained 8 T-residues, etc. [in the present figure, the sequence with SEQ ID: 1 shows for the sake of illustration the sequence of the template to better illustrate the one ne difference between primer and template. In reality the sequence will be complementary to the template, apart from the one under consideration to achieve the effect of the invention].

FIG. 5a: Example, in accordance with an embodiment of methods of the present invention as shown in FIG. 4, wherein a sequence tag (a given nucleotide sequence) is added to the primers as adapters. Standard PCR primers (one or both) may contain one type of adapter, while the primers used in hnrPCR (one or both) may contain another type of tag. If more than one amplicon is generated in a multiplex (-like) PCR, the tags of the primers used for generation of the 'standard'-amplicons may be identical or not. If more than one hnr-amplicon is generated in a multiplex(-like) format, the tags of the hnr-primers may be identical or not. In this way all amplicons can be combined and separated for analysis. In this example, standard PCR and hnr-PCR are performed in parallel in which both primers used for generation of the hnr-amplicon are different from the primers used for generation of the standard amplicon.

FIG. 5c: Example, in accordance with an embodiment of methods of the present invention as shown in FIG. 4, wherein a sequence tag (a given nucleotide sequence) is added to the primers as adapters. Standard PCR primers (one or both) may contain one type of adapter, while the hnr-primer for generation of the hnr-amplicon contains another type of tag. If more than one amplicon is generated in a multiplex(-like) PCR, the tags of the primers used for generation of the 'standard'-amplicons may be identical or not. If more than one hnr-amplicon is generated in a multiplex(-like) format, the tags of the hnr-primers may be identical or not. In this way all amplicons can be combined and separated for analysis. In this example, the PCR reaction is first performed with classical primers only. At the end of the PCR reaction, the hnr-primer(s) is(are) added. Here, PCR products of the classical PCR reaction become the template of the hnr-primers, when the amplification is continued for 1 or more additional temperature cycles.

DETAILED DESCRIPTION OF THE INVENTION

Different sequencing technologies use different technologies for determining the nucleotide sequence of a DNA strand. A common feature of current high throughput sequencing technologies is that many DNA strands are sequenced in parallel, mostly on the surface of a small plate (picotiterplate, flow cell), yielding up to more than 600 Gb (giga bases) sequence information. Typically, these DNA fragments carry identical sequence ends, e.g. through the linking of small nucleotide adapters during the DNA preparation phase for sequencing, so that the same primer can be used for the sequencing of all DNA fragments in parallel.

Current high throughput sequencing technologies can be broadly divided into two categories on the basis by which sequencing is performed; sequencing by synthesis (Illumina, Roche, Ion Torrent, Helicos and Pacific Biosciences) and sequencing by ligation (SOLID, Life Technologies).

Sequencing by synthesis can be further divided into two distinct categories. In the first subcategory, each incorporated nucleotide is detected as such, such as in the reversible terminator approach in which each nucleotide is labelled with a different fluorophore and a single base elongation with any base is assayed concurrently. Only one single base incorporation is possible in each cycle/step of the sequencing reaction. Indeed, the nucleotides are protected, such that they can be incorporated in a growing DNA strand, but once incorporated, another nucleotide cannot be incorporated in the same cycle/step. In a new cycle, the incorporated nucleotide of the previous cycle is first deprotected, so that one new protected nucleotide can be incorporated in the new cycle. In the second subcategory, a side product of nucleotide incorporation is monitored, such as pyrophosphate in pyrosequencing or a proton in Ion Semiconductor Sequencing. In both the latter strategies, individual native nucleotides are added sequentially. Pyrosequencing or Ion Semiconductor Sequencing follows DNA polymerase progression along a DNA strand by allowing only a single dNTP to be available for incorporation in a given cycle, and then takes advantage of the chemical reaction that occurs when the dNTP is incorporated by the polymerase. This reaction is detected either by inducing a bioluminescence cascade starting from pyrophosphate and detecting the emitted light (pyrosequencing), or by directly detecting protons released during incorporation as a change in pH (Ion Semiconductor Sequencing). A new cycle is then started for another dNTP. The four different dNTPs are thus separately added in four different cycles, and this is repeated for a given number of rounds, in which each round is built up of the same order of 4 cycles of administration of the 4 different dNTPs.

More specifically for pyrosequencing, a sequencing primer is hybridized to a single stranded DNA template and incubated with the enzymes DNA polymerase, ATP sulfurylase, luciferase, the substrates adenosine 5' phosphosulfate (APS) and luciferin. The addition of one of the four deoxynucleotide triphosphates (dNTPs) (dATP is not used, but rather dATPaS which is not a substrate for luciferase) initiates the second step. DNA polymerase incorporates only the given dNTP if it is complementary onto the template. This incorporation releases pyrophosphate (PPi) stoichiometrically. ATP sulfurylase then quantitatively converts PPi to ATP in the presence of adenosine 5' phosphosulfate. This ATP acts as fuel to the luciferase-mediated conversion of luciferin to oxyluciferin that generates visible light in amounts that is proportional to the amount of ATP. The light produced in the luciferase catalyzed reaction is detected by a camera and analyzed in a program. Unincorporated nucleotides and ATP are then degraded by apyrase, and the reaction can restart with another nucleotide. The four DNA nucleotides are added sequentially in a fixed order across the picotiterplate. During the nucleotide flow, thousands of copies of DNA bound to each of the beads are sequenced in parallel. When a nucleotide complementary to the template strand is added into a well, the polymerase thus extends the existing DNA strand by adding nucleotide(s). In case that the template carries a stretch of identical nucleotides, a number of nucleotides equal to the length of the stretch can be incorporated in the same cycle/step. Indeed, native unprotected dNTPs are used, so that more than one nucleotide can be incorporated in a given cycle. The signal strength is proportional to the number of nucleotides. The signal strength for homopolymer stretches, however, is only linear up to seven consecutive nucleotides. The sequence of solutions which produce chemiluminescent signals allows the determination of the sequence of the template in the end.

More specifically for Ion Semiconductor Sequencing, a microwell containing clonal template DNA strands on a bead is flooded with a single species of deoxyribonucleotide (dNTP). If the introduced dNTP is complementary to the leading template, the nucleotide is incorporated into the growing complementary strand. This causes the release of a hydrogen ion that triggers a hypersensitive ion sensor, which indicates that a reaction has occurred. If the introduced dNTP is not complementary to the leading template nucleotide, no nucleotide is incorporated and no hydrogen ions are released. The chip is sequentially flooded with one nucleotide after another. Again here, since native unprotected dNTPs are used, multiple dNTP molecules will be incorporated in a single cycle at homonucleotide stretches. This leads to a corresponding number of released hydrogens and a proportionally higher electronic signal. Again here, the accuracy of correct calling of the number of nucleotides in homonucleotide stretches decreases for longer homonucleotide stretches.

The Ion Semiconductor Sequencing technology differs from other sequencing technologies in that no optics is used. Ion semiconductor sequencing may also be referred to as Ion Torrent sequencing, pH-mediated sequencing, silicon sequencing, or semiconductor sequencing. Ion Semiconductor Sequencing creates a direct connection between the chemical and the digital worlds, enabling fast, simple, massively scalable sequencing. Ion Semiconductor Sequencing Chips are designed, manufactured and packaged like any other semiconductor chips. Wafers are cut from a silicon boule. The transistors and circuits are then pattern-transferred and subsequently etched onto the wafers using photolithography. This process is repeated 20 times or more, creating a multi-layer system of circuits. Ion Semiconductor sequencing benefits from four decades of exponential improvement in semiconductor technology, also known as Moore's Law.

Pyrosequencing and Ion Semiconductor Sequencing allows sequencing to proceed at a much faster rate than e.g. reversible terminator sequencing, because fewer steps are required to detect a base and to continue the extension of a template. As such, it is common to achieve currently 100-basepair reads in fewer than 3 h with pyrosequencing or Ion Semiconductor Sequencing. Moreover, longer sequence reads can be obtained in pyrosequencing and Ion Semiconductor sequencing, of which the templates can be generated by classical PCR amplification. In diagnostics this is highly desirable, since PCR is much less labor-intensive then other template preparation technologies such as the construction of DNA libraries. Another plus of the preparation of sequencing template by PCR is that the standard length of obtained amplicons, as well as the read lengths obtained with these sequencing technologies, are in the range of the size, or over the size, of the average length of exons. Therefore the number of amplicons needed for the sequencing of a given gene is of the same order of the exons in most genes, so that most amplicons cover single exons. When performed in a multiplex format, all exons of interest can be enriched in one or a limited number of steps. This can also be achieved in a multiplex-like format, such as highly parallel amplification on integrated fluidic circuits (Fluidigm). Indeed, although each PCR reactor of the integrated fluidic circuit generates only one type of amplicon, the parallel nature of the integrated fluidic circuit achieves and assures a multiplex-like format.

These sequencing formats, especially Ion Semiconductor Sequencing, has the highest potential to become the most important sequencing format in future routine genetics tests, especially tests in which only one or a few genes are analyzed. The inaccurate calling of (longer) homonucleotide stretches, however, is a serious pitfall. Especially homonucleotide stretches of 7 nucleotides long, or longer, are not always correctly called. Most genes carry at least 1 or a few homonucleotide-stretches in this size range. Moreover, homonucleotide stretches are prone to mutations, e.g. because of slippage of DNA polymerase. A correct characterization of homonucleotide stretches is therefore a prerequisite for a diagnostic test that aims to analyze complete regions of a genome, such as (a) gene(s). For example, the coding region and exon/intron junctions of the CFTR gene, in which mutations cause cystic fibrosis, contains three homonucleotide stretches of at least 7 nucleotides. Most commercial CFTR tests, the most common genetic tests performed in the Caucasian population and which are so far not based on sequencing, only screen for about the 30 most common CFTR mutations, which include three mutant loci located in these homonucleotide stretches. The pitfall of inaccurate characterization of homonucleotide stretches thus prohibits the implementation of pyrosequencing and Ion Semiconductor Sequencing in routine genetic diagnostics. Indeed, either no accurate typing can be performed at these homonucleotide-stretches, or a second assay such as classical Sanger is performed across these problematic homonucleotide-stretches. This is not desirable in routine genetic testing, and a 'one-stop' or 'one-shop' test is preferred.

For most routine diagnostic genetic tests, there is only an interest in the analysis of one or a few genes. In fact, only the exons and exon/intron junctions of these genes are characterized. These DNA regions of interest are therefore first enriched from the total genome in order to reduce the 'background signal' of DNA regions not of interest, and to increase the sensitivity of detection.

Neighboring nucleotide positions in a DNA molecule may harbor a(n) identical nucleotide(s). In the context of the present invention a repeat of identical nucleotides is also called a "homonucleotide stretch". A repeat can have as little as 2 or 3 identical nucleotides, and can extend up to more than 15 to identical nucleotides. Repeats of 7, 8, 9 or 10 are more common, repeats of more than 15 are less common. Because of unpredictable structural conformations, some repeats of 5 or 6 repeats may be even difficult to type. Particular embodiments include ranges having as lower and upper limit any of the above cited values, For example, 7 T-nucleotides in a row would thus be called a homonucleotide stretch of 7 nucleotides.

Figure 2:
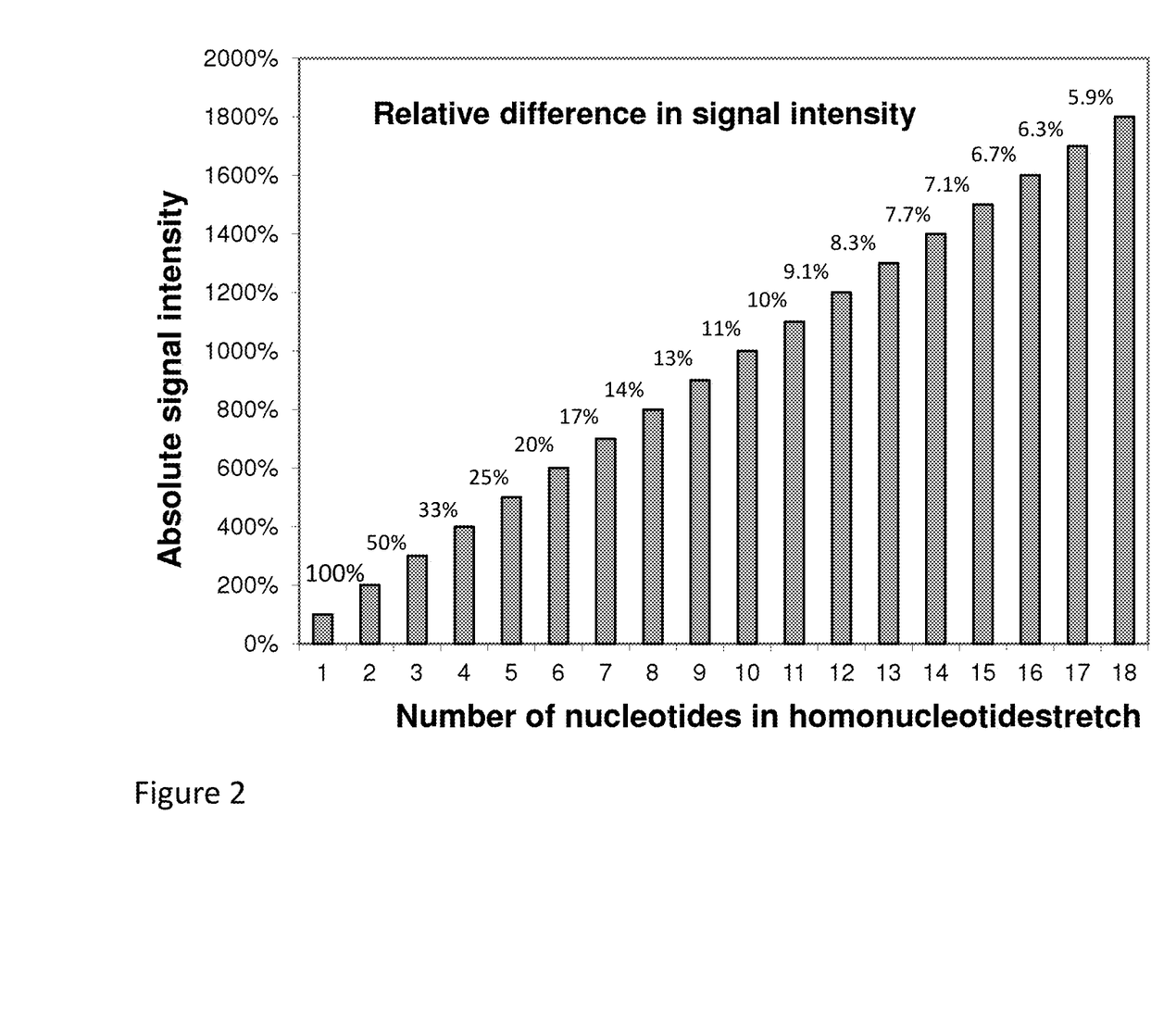
FIG. 2: Absolute and relative signal differences obtained in assays such a pyrosequencing and Ion Semiconductor Sequencing of different homonucleotide stretches.

In pyrosequencing and Ion Semiconductor sequencing, native (unprotected) nucleotides are added to the sequencing reaction in each cycle. At a given homonucleotide-stretch, more than 1 nucleotide will thus be incorporated in a sequencing reaction. The number of complementary nucleotides that will be incorporated equals the number of nucleotides in the homonucleotide stretch, so that the signal strength is proportional to the number of nucleotides. The signal strength for homopolymer stretches, however, is only linear up to seven consecutive nucleotides. Indeed, the longer the homonucleotide stretch, the smaller the difference in signal intensity for 1 less or 1 more nucleotide in the homonucleotide stretch (FIG. 2). For example, a 3-homonucleotide stretch results in a 50% higher signal then a 2-homonucleotide stretch, while a 8-homonucleotide stretch only results in a 14% higher signal then a 7-homonucleotide stretch. At a given moment, the signal difference that needs to be detected in order to determine the exact length of a homonucleotide-stretch is of the same order as the variability in background signal, so that the system reaches its limit of detection of signal differences. Some shorter homonucleotide stretches than 7 nucleotides might even incorrectly called since sequence-context specific secondary structures may hamper DNA polymerization.

In this invention, the longer homonucleotide stretch which cannot be accurately determined is reduced to two, or more (e.g. 3, 4, 5 or 6), smaller parts, in which at least the 3' part can each be accurately determined in sequencing assays, such as pyrosequencing and Ion Semiconductor sequencing. Only the last one of the repeats needs to be in this range of less than 5 to 7 identical nucleotides, the first one may still be more than 5 to 7 nt, since the first one is completely located in the oligonucleotide and should have the expected number when well synthesized and purified. However, to control for lower quality oligo's, a very long stretch might be reduced to more than 2 parts so that they are all less than 5 to 7 nt long so that they can be counted as an extra control. Their combined length then allows an accurate determination of the original longer homonucleotide stretch. Typically only the last smaller homonucleotide-stretch thus has a length that can be typed at the highest accuracy.

The reduction in homonucleotide stretch can be achieved in a DNA synthesis reaction, which is defined in this invention as 'homonucleotide-stretch-reduction (hnr) DNA synthesis'. When a PCR reaction is used for DNA synthesis/amplification, the technique is defined in this invention as "homonucleotide-stretch-reduction PCR" (hnr-PCR).

In fact, in order to obtain sufficient strong sequencing signals and/or to sequence specific regions of the total genome only, the DNA molecules to be sequenced have to be enriched by copying or even amplification. hnr-PCR can be a means of copying/amplification so that the homonucleotide stretch reduction and amplification of DNA target can be performed at the same time in a single step.

Figure 3:
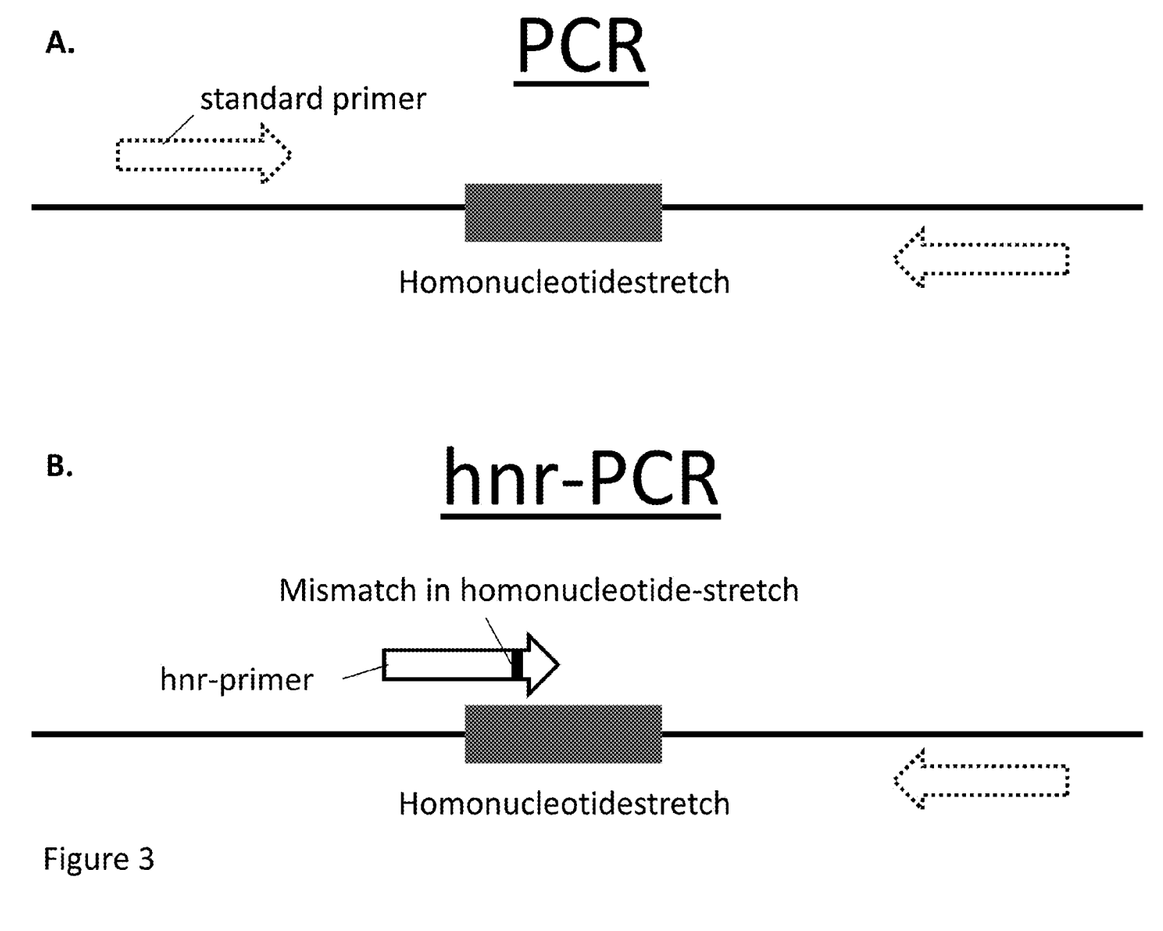
FIG. 3: A. Standard PCR in which the primers, indicated by arrows, flank the region of interest, in this case a region which contains a homonucleotide stretch. [prior art] B. hnr-PCR, in accordance with an embodiment of methods of the present invention, in which one of the primers extends in the homonucleotide stretch of interest. This hnr-primer contains one or more mismatches with the homonucleotide stretch.

For amplification, primers are designed so that they bind to their complementary target DNA through hybridization. Primers are normally designed to be 100% complementary to their target DNA. However, even a primer that is not 100% complementary may bind to its target DNA region, especially when DNA synthesis is performed in less stringent conditions. A new DNA strand is then synthesized through extension of the 3' end of the primer. Although a primer needs not to be 100% complementary in order to prime DNA synthesis, the 3' nucleotide needs to be 100% complementary and be hydrogen-bounded with its DNA target in order to initiate the synthesis of a new DNA strand. For hnr-PCR, an hnr-primer can be designed at a homonucleotide stretch which extends in the homonucleotide-stretch (FIGS. 3 and 4), either partly in the homonucleotide stretch or until its complete end. Of course, the primer preferably needs to contain more unique complementary sequences 5' preceding the targeted homo-nucleotide-stretch in order to increase the specificity of binding. In practice, additional adapter sequences may be added 5', to allow further processing of the newly synthesized DNA strands such as adapter sequences for primer needed in sequencing, second PCR steps, emulsion-PCR, barcode sequences, etc. The 3' end of an hnr-primer will thus harbor a homonucleotide stretch, or even 1 nucleotide, in which the nucleotide type is complementary to the nucleotide type in the target homonucleotide stretch. Since a primer needs not to be necessarily 100% complementary to its target region, non-complementary nucleotides can be incorporated at certain positions to obtain an hnr-primer, e.g. the 2nd last 3' position of the hnr-primer, the 3rd last 3' position of the hnr-primer, etc. . . . (in this context the nucleotide at the 3' end is at the "first" 3' position"). When one nucleotide is substituted for a non-complementary nucleotide in the region of the homo-nucleotide-stretch, the homonucleotide-stretch gets disrupted and split in two smaller parts so that the original homo-nucleotide-stretch is reduced to two smaller parts. The two parts might be either two smaller homonucleotide stretches of the same length, or not. The 3' part might even become one nucleotide long, and may thus even not be a homonucleotide stretch anymore. An hnr-primer which does not extend until the end of the homonucleotide stretch will detect deletions and insertions in the homonucleotide stretch. An hnr-primer which does extend until the end of the hornonucleotide stretch will detect insertions, but not deletions in the homonucleotide stretch.

The present invention accordingly differs from prior art methods wherein the poly A sequence in a cDNA is amplified with a primer comprising a mismatch with this poly A stretch. In the present invention the primer has at the 5' end a sequence which hybridizes with the non-repetitive part of the template DNA.

The present invention can be applied on DNA targets with a poly A homonucleotide-stretch but equally on poly C, poly G and poly T homonucleotide-stretches.

For example, for a homonucleotide stretch of 8 nucleotides, an hnr-primer which extends 6 nucleotides in the homonucleotide-stretch and in which the second last nucleotide of the hnr-PCR is substituted by a non-complementary nucleotide, a newly synthesized DNA strand will contain a 4-homonucleotide stretch, followed by the non-complementary nucleotide, and followed by a 3-homonucleotide stretch. If a sequencing reaction detects at this last position a homonucleotide-stretch of 3 nucleotides long, the DNA fragment under investigation then harbors 8 nucleotides in the original homonucleotide stretch. If a sequencing reaction detects at this position a homonucleotide stretch of 2 nucleotides long, the DNA fragment under investigation then harbours 7 nucleotides in the homonucleotide stretch. And if a sequencing reaction detects at this position a homonucleotide stretch of 4 nucleotides long, the DNA fragment under investigation then harbors 9 nucleotides in the homonucleotide stretch. In this way, and in this example, the inaccurate calling of 7, 8 or 9 nucleotides in a homonucleotide stretch is transformed to an accurate calling of 2, 3 or 4 nucleotides respectively.

In another example, for a homonucleotide stretch of 8 nucleotides, an hnr-primer which extends until the end of the homonucleotide-stretch and in which the second last nucleotide of the hnr-PCR is substituted by a non-complementary nucleotide, a newly synthesized DNA strand will contain a 6-homonucleotide stretch, followed by the non-complementary nucleotide, and 1 nucleotide of the same type as the 6-homonucleotide stretch.

In another example, for a homonucleotide stretch of 8 nucleotides, an hnr-primer which extends 7 nucleotides in the homonucleotide-stretch and in which the third last nucleotide of the hnr-PCR is substituted by a non-complementary nucleotide, a newly synthesized DNA strand will contain a 4-homonucleotide stretch, followed by the non-complementary nucleotide, and followed by a 3-homonucleotide stretch.

More than 1 nucleotide mismatch can be incorporated at regularly intervals in a hnr-primer, so that different smaller homonucleotide stretches are obtained as a further control. For a homonucleotide stretch of 15 nucleotides in which the $5^{th}$ and $12^{th}$ nucleotide is mismatched in the hnr-primer, the 15-homonucleotide stretch will be reduced to two 5-homonucleotide stretches and a third 3-homonucleotide stretch.

Of course, sequencing reactions of such hnr-amplicons provide no information about potential mutations at the site of the primer, since the observed sequenced sequence at that site is derived from the primer instead of the target DNA under investigation. In the example above in which an 8 nucleotide long homonucleotide stretch is reduced by hnr-PCR, in which the hnr-primer extends 6 nucleotides in the homonucleotide-stretch and in which the second last nucleotide of the hnr-PCR is substituted by a non-complementary nucleotide, the 4 nucleotides of the first smaller homonucleotide stretch, the mismatched nucleotide, and the first nucleotide of the second 3-homonucleotide stretch, does not provide sequence information of the DNA fragment under investigation since it is derived from primer sequence. The second and third nucleotide of the second 3-homonucleotide stretch, however, does provide sequence information of the DNA under investigation. Also for this reason it may be preferable that hnr-primers do not extend until the complete end of the homonucleotide stretch, so that sequence information is obtained of the junction of the homonucleotide stretch.

In many instances, the sequence nevertheless needs to be determined at the site of the hnr-primer or even upstream. Indeed, in many instances, a homonucleotide stretch is located somewhere in an exon, and the complete sequence of the exon and exon/intron junctions needs to be determined. Therefore, a classical PCR amplification may also be performed using primers flanking the complete region of interest, including the homonucleotide stretch (FIG. 3). hnr-PCR might thus be used as such, or in combination with classical PCR.

There are different ways to combine hnr-DNA synthesis with a classical DNA synthesis reaction. We describe here the different options for hnr-PCR for one amplicon with a classical PCR for one amplicon; however it applies to all DNA synthesis reactions for a person familiar with the art, either in singleplex or multiplex format.

In a first format, hnr-PCR and classical PCR will be performed in parallel, i.e. the classical PCR primers will be combined in one tube, while the hnr-PCR primers in another tube, and will be separately amplified, after which the hnr-PCR amplicons and classical amplicons are combined for further sequencing. For hnr-PCR, the non-hnr-primer may be different (FIG. 5a) or identical (FIG. 5b) to one of the two classical PCR primers.

In a second format, all hnr-primers and classical PCR primers are combined in one reaction (i.e. 4 different primers per target if the non-hnr-primer for the hnr-amplicon is different from one of the two classical PCR primers, or 3 different primers if the non-hnr-primer for the hnr-amplicon is identical to one of the two classical PCR primers). Given that there are then 2 directional primers, and possibly even 2 anti-directional primers, different types of amplicons can be generated depending on which primer is incorporated, which may affect the efficiency of the DNA amplification. Preferential use of either the classical or hnr-PCR primer in a given step of an assay might be obtained by differences in melting temperature of (a) given primer(s) so that they can be differently called in the PCR temperature profile, and/or they may added at different concentrations and in this way one primer may be selected over the other depending on the concentration, or a combination of a difference in melting temperature and concentration.

Figure 5A:
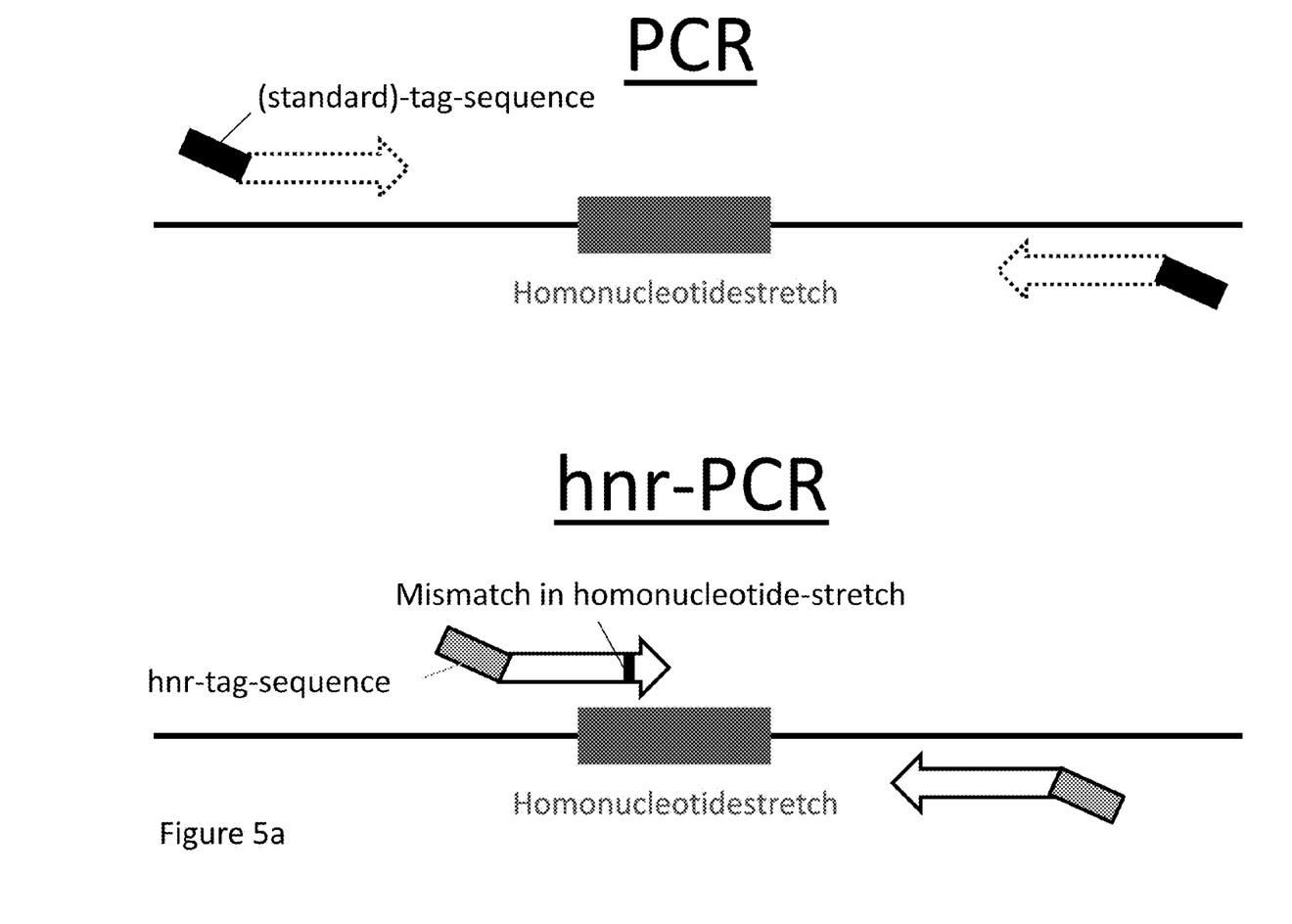
FIG. 5b: Same as 5a, in which standard PCR and hnr-PCR are performed in parallel but in which the non-hnr-primer for generation of the hnr-amplicon is identical to one of the classical primers for generation of the standard amplicon.
Figure 5B:
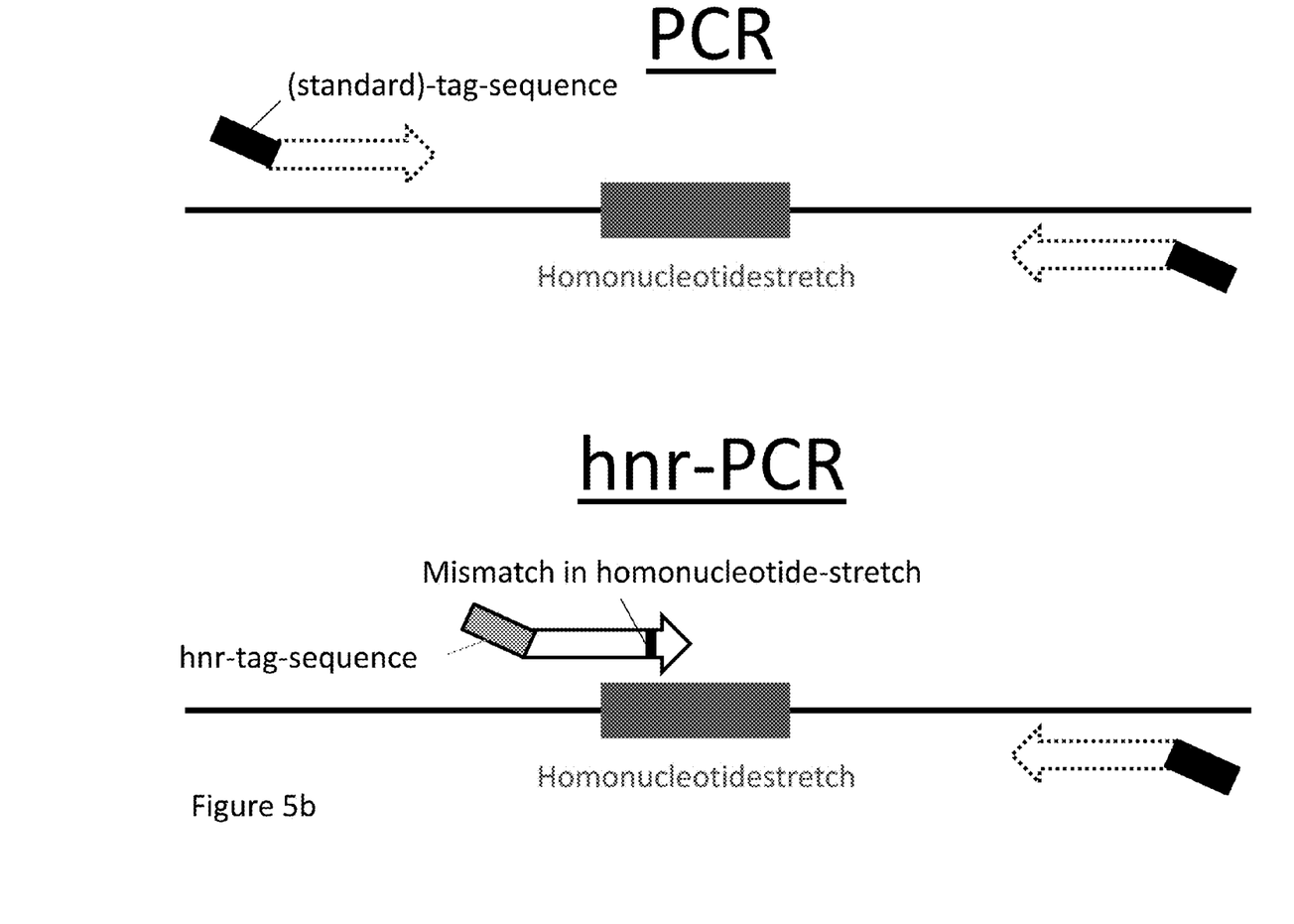
Figure 5C:
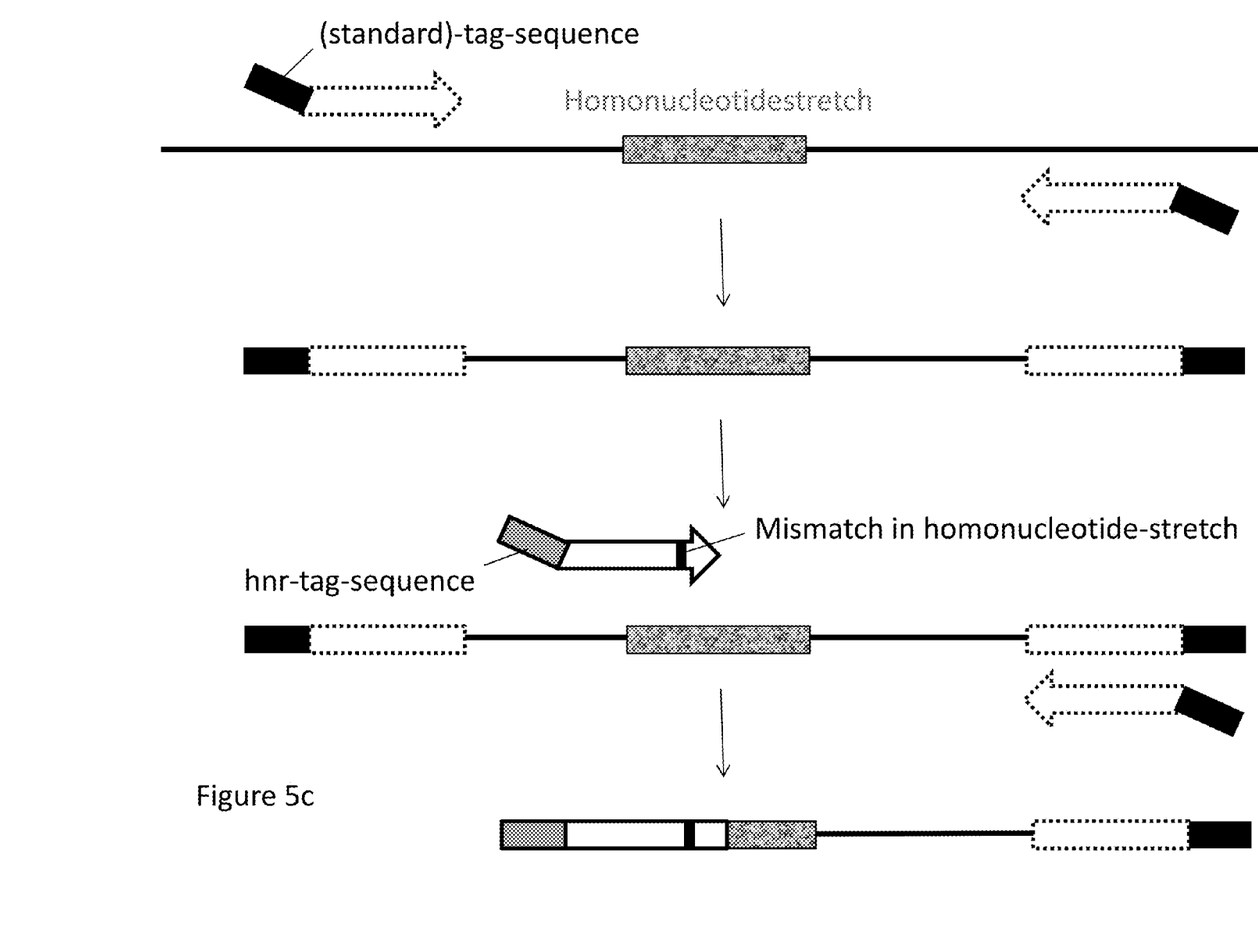

In a third format, primers are added serially and DNA synthesis reactions are performed serially (FIG. 5c). More specifically, the PCR reaction is first performed with classical primers only. At the end of the PCR reaction, the hnr-primer(s) are added. Here, PCR products of the classical PCR reaction become the template of the hnr-primer. Since the amount of DNA products doubles after each PCR cycle, only 1 or a few additional temperature cycles will be needed for generating sufficient hnr-amplicons once that the hnr-primer(s) have been added to the classical PCR reaction templates. Moreover, since the generated PCR template is amplified/enriched and therefore becomes a more homogeneous template than the original total genomic DNA used in a PCR reaction, an hnr-PCR primer has a much higher probability of hybridizing specifically to a generated classical PCR amplicon than aspecifically in the complex total genomic DNA outside the target regions. In this way less aspecific amplification products will be generated. Given that the hnr-primer has already at least one mismatch and is therefore less stringent, and that the hnr-primer needs to be positioned at the homonucleotide stretch so that there are less options for design of the most optimal specific primer, a serial format may even make an hnr-PCR reaction more efficient and specific. Once that the hnr-primer is added at the classical PCR solution, the hnr-primer may compete with the other primers. Again here, the hnr-primer may have a higher probability for priming over the other primers, because of a favorable melting temperature and/or concentration. If present in a higher concentration, it has a higher probability for priming over the primers that are present in a lower concentration.

To a person skilled in the art it is obvious that hnr-primers can be added combined together, serial or parallel, to any DNA synthesis or DNA amplification protocol.

Any DNA molecule can be a template for hnr-DNA synthesis (or hnr-PCR), i.e. genomic DNA, a modified genomic DNA fragment (e.g. a DNA library prepared from genomic DNA in which DNA was fragmented, ligated to adapters, etc. as is done in standard nextgen sequencing), or an amplified fragment (classical amplicon).

The combined analysis of a standard amplicon and hnr-amplicon against a given region will then conclude the actual sequence, in which the standard amplicon provides the qualitative information of the sequence, except the exact length of the homonucleotide stretch, while the hnr-amplicon will determine the exact length of the homonucleotide stretch.

One single type of hnr-fragment, or homonucleotide stretch, might be generated and analyzed, and therefore a single pair of primers is used. On the other hand, a combination of different types of hnr-fragments, directed against different homonucleotide stretches may be generated and analysed in a multiplex(-like) format in which multiple pairs of primers are used. In such a multiplex-format, even the respective standard amplicons might be included, such as amplicons containing the complete homonucleotide stretches under investigation When multiplex-(like) PCR formats are used in which standard amplicons and hnr-amplicons are amplified together, the non-hnr-primer used for generation of the hnr-amplicon might be either the same, or not the same, as the one used for the amplification of the respective standard amplicon.

Figure 6:
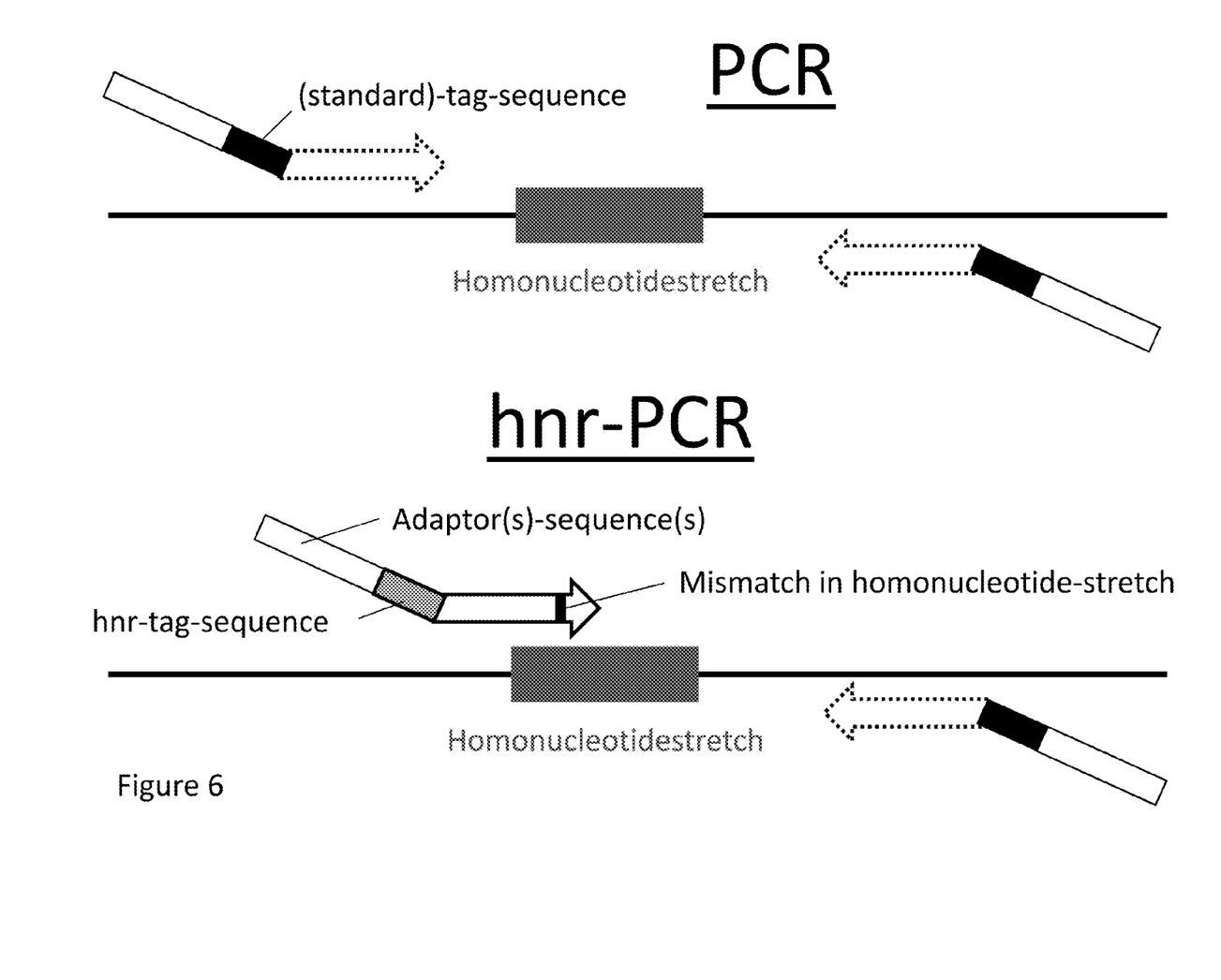
FIG. 6: Example in accordance with an embodiment of methods of the present invention as shown in FIG. 5b, wherein one or more adapter sequences or attached to the primers for further processing, such as a priming site for a second DNA synthesis or PCR, sequencing, barcode, etc., or a combination thereof.

In new generation sequencing technologies many sequence reads need to be analyzed at any position and need to be aligned to the reference sequence. Indeed, the analysis has a probabilistic nature and these sequencing technologies have a relatively high sequencing error per sequencing read. Typically, every nucleotide in a sequence under investigation needs to be detected in 20 to 30 sequence reads to deduce a diploid sequence with a high accuracy. Moreover, all sequences of multiple amplicons or DNA targets are generated in a single experiment and a mixture of sequence reads of all these amplicons will be obtained. Typically, a mixture of reads derived from a mixture of amplicons derived from different targets, such as all exons of a gene, are obtained. When standard amplicons and hnr-amplicons to the same target are combined, the obtained mixture will be even more complex and will contain for a given homonucleotide stretch both sequence reads obtained from standard PCR amplicons and reads from hnr-PCR amplicons. Apart from their difference in length (the hnr-PCR amplicon only starts or ends around the homonucleotide stretch sequence), the hnr-amplicon contains one or more intently introduced mismatched nucleotide(s) which behave as (a) point mutation(s). When standard amplicons and hnr-amplicons are aligned together, both types of amplicons will correctly align to the reference sequence, and the mismatched nucleotide will be wrongly called as a mutation. The standard amplicons and hnr-amplicons thus need to be separated for analysis and separately aligned so that their alignment and analysis does not interfere. This can be easily realized when different 5' adapter sequences are introduced in the primer used for standard amplification and hnr-amplification (FIGS. 5a-c). Although the adapter sequences may differ for each amplicon, all standard amplicons preferably contain the same adapter sequence, and if more than one homonucleotide stretch needs to be analyzed by hnr-PCR, all hnr-amplicons preferably contain a same different adapter sequence. The pool of obtained sequence reads may then be separated in two pools based on the adapter sequence, so that a pool of standard amplicons and a pool of hnr-amplicons is obtained. Each pool will then be separately aligned to the reference sequence so that their alignment and analysis does not interfere. Preferably the reference sequence for the homonucleotide stretch may be adapted so that the mismatched nucleotide is taken up in the reference sequence. To all primers, both standard primers and hnr-primers, additional adapter sequences may be added for further processing, such as sequences for oligonucleotide hybridization for another amplification, sequencing, and barcode sequences (FIG. 6).

In the context of the present application, PCR, and therefore hnr-PCR is typically the method of hnr-DNA-synthesis. However the methods of the present invention can be performed with any technique that syntheses one or more new DNA strands from an original DNA strand. Suitable methods known in the art are for example, isothermal amplification (rolling circle amplification), single strand displacement amplification, nucleic acid sequence-based amplification (NASBA), solid phase PCR (on beads or arrays) (Raindance), padlock probes, selector probes, collector probes, Haloplex PCR (Halogenomics), ligase chain reaction and amplification of 'extension-ligation of bound oligos'-products (TSCA; TruSeq Custom Amplicon, Illumina), etc., or a combination thereof.

The invention claimed is:

1. A method of generating one or more copies of a target DNA molecule, or part thereof, that contains a repeat of identical nucleotides, comprising the steps of:
   altering one nucleotide in this repeat of identical nucleotides, or
   altering different single nucleotides separated at intervals in said repeat of identical nucleotides into another nucleotide, in order to reduce said repeat of identical nucleotides into two or more smaller altered parts of said identical nucleotides in the copied molecules,
   wherein the alteration is performed by amplification with an oligonucleotide primer comprising at the 5' side a sequence which hybridizes with the sequence preceding the targeted sequence repeat, and comprising at the 3' side a sequence which hybridizes with the targeted sequence repeat, wherein the sequence which hybridizes with the targeted sequence repeat is not 100% complementary with said repeat.

2. The method according to claim 1, wherein the two or more smaller altered parts are no longer than 4, 5 or 6 nucleotides.

3. The method according to claim 1, wherein said 3' side of said oligonucleotide primer hybridizes with a part of the targeted sequence repeat.

4. The method according to claim 1, wherein the smaller altered parts of identical nucleotides are generated through an enzymatic or chemical reaction, selected from the group consisting of DNA synthesis, ligation, and/or amplification, and a combination thereof.

5. The method according to claim 1, wherein the repeat of identical nucleotides at the 3' end of the primer is shorter than the repeat of identical nucleotides at the 5' end of the primer.

6. The method according to claim 1, wherein the nucleotide in the repeat of complementary identical nucleotides of the primer which is replaced by another nucleotide type is at the second, third, fourth, or fifth position counted from the 3' end of the oligonucleotide primer.

7. The method according to claim 1, wherein the primer contains in addition at the 5' end one or more adapter nucleotides which are not complementary to the target DNA molecule.

8. The method according to claim 1 further comprising the simultaneous amplification of said target DNA molecule comprising said repeat of identical nucleotides with primers flanking the repeat of identical nucleotides.

9. The method according to claim 1, further comprising amplification of the target DNA, including the repeat of identical nucleotides.

10. The method according to claim 8, further comprising determining the sequence of said target DNA molecule with primers flanking the repeat of identical nucleotides of said one or more copies, generated by amplification with the oligonucleotide primer which extends in the unaltered repeat of identical nucleotides of the target DNA, and determining the sequence of the amplified target DNA, including the repeat of identical nucleotides, and comprising the step of analyzing the determined sequence of the altered repeats and the corresponding sequence of the unaltered sequence.

11. The method according to claim 8, wherein said method is simultaneously performed on more than one repeat of identical nucleotides and on more than one target DNA, including the repeat of identical nucleotides.

12. The method according to claim 8, wherein the oligonucleotide used to perform the alteration in the repeat of identical nucleotides is added after said amplification of said target DNA has been performed or partly performed.

* * * * *

SEQUENCE LISTING

<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: PCR primer

<400> SEQUENCE: 1
ggaacgcgtc acgtttat                                                18

<210> SEQ ID NO 2
<211> LENGTH: 52
<212> TYPE: DNA
<213> ORGANISM: Artificial Sequence
<220> FEATURE:
<223> OTHER INFORMATION: theoretical DNA template

<400> SEQUENCE: 2
tggaggtagc ctaggaacgc gtcacgtttt tttttgatgg acctagtggc at           52

<210> SEQ ID NO 3
<211> LENGTH: 39
<212> TYPE: DNA
<213> ORGANISM: Artificial Sequence
<220> FEATURE:
<223> OTHER INFORMATION: modified hypothetical new DNA strand

<400> SEQUENCE: 3
ggaacgcgtc acgtttattt tgatggacc tagtggcat                          39